US009931506B2

United States Patent
Chung et al.

(10) Patent No.: US 9,931,506 B2
(45) Date of Patent: Apr. 3, 2018

(54) ARTIFICIAL RETINAL PROSTHESIS SYSTEM, OPTICAL DEVICE AND RETINA CHIP

(71) Applicant: NATIONAL CHIAO TUNG UNIVERSITY, Hsinchu (TW)

(72) Inventors: Jung-Chen Chung, Hsinchu (TW); Wei-Ming Chen, Hsinchu (TW); Chung-Yu Wu, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 160 days.

(21) Appl. No.: 14/950,580

(22) Filed: Nov. 24, 2015

(65) Prior Publication Data

US 2017/0007835 A1 Jan. 12, 2017

(30) Foreign Application Priority Data

Jul. 8, 2015 (TW) .............................. 104122099 A

(51) Int. Cl.
*A61F 2/16* (2006.01)
*A61N 1/36* (2006.01)
*G06K 9/00* (2006.01)
*A61N 1/378* (2006.01)
*A61N 1/372* (2006.01)
*A61N 1/05* (2006.01)

(52) U.S. Cl.
CPC ....... *A61N 1/36046* (2013.01); *A61N 1/3787* (2013.01); *A61N 1/37217* (2013.01); *G06K 9/00604* (2013.01); *A61N 1/0543* (2013.01)

(58) Field of Classification Search
CPC .......... A61F 2/14; A61F 9/08; A61F 9/00727; A61N 1/36046; A61N 1/0543
USPC ........................................................ 623/6.63
See application file for complete search history.

(56) References Cited

U.S. PATENT DOCUMENTS

2005/0090875 A1   4/2005   Palanker et al.

FOREIGN PATENT DOCUMENTS

TW           201334768 A       9/2013

*Primary Examiner* — Thomas J Sweet
*Assistant Examiner* — Tiffany Shipmon
(74) *Attorney, Agent, or Firm* — Muncy, Geissler, Olds & Lowe, P.C.

(57) ABSTRACT

An artificial retinal prosthesis system comprises an extraocular optical device and an intraocular retina chip. The extraocular optical device receives an external image, converts it into an optical pulse signal, and generates light energy. The intraocular retina chip receives the optical pulse signal from the extraocular optical device and produces an electric simulation signal. The intraocular retina chip includes a solar cell module receiving and converting the light energy into electric energy as a power source of the intraocular retina chip. The artificial retinal prosthesis system uses an optical modulation method to convert an image signal into an optical pulse signal, transmits the optical pulse signal into the eyeball, and decodes the optical pulse signal intraocularly. Thereby, the signal light intensity is improved without affect the contrast ratio.

6 Claims, 3 Drawing Sheets

ARTIFICIAL RETINAL PROSTHESIS SYSTEM, OPTICAL DEVICE AND RETINA CHIP

BACKGROUND OF THE INVENTION

1. Field of the Invention

The present invention relates to an artificial retinal prosthesis system, an optical device and a retina chip, particularly to an artificial retinal prosthesis system, an extraocular optical device and an intraocular retina chip, which use an optical modulation method to convert image information into optical pulse signals.

2. Description of the Prior Art

Retinitis pigmentosa and age-related macular degradation (AMD) are diseases caused by degradation of retinal photoreceptor cells. AMD is likely to occur in aged persons. Statistic data shows that 0.8% adults aged over 40 suffer AMD and risk blindness in USA. The patients blinded by the abovementioned diseases are hard to treat with drugs. However, the researches about replacing photoreceptor cells with an artificial retina have brought much hope to the related patients.

The conventional artificial retina is powered by a solar chip and uses electricity to stimulate the residual nerve cells and generate vision. However, the related technologies normally suffer from a problem that solar chips are hard to provide sufficient power. A U.S. patent No. US20050090875 disclosed a head-wearable background light projector, which projects intense light to the intraocular retina chip to make the photocells output more power. However, the prior art decreases image contrast and degrades image quality. A Taiwan patent No. TW201334768 uses a background light eliminator to overcome the problem that the background light decreases contrast. However, the prior art needs a high-precision focusing system because the intraocular retina chip is very small. Besides, imaging light is not allowed to project to the background light eliminator. Otherwise, the signal light would be eliminated, and the image quality would be degraded. Therefore, an artificial retina technology is required to overcome the abovementioned problems.

SUMMARY OF THE INVENTION

The present invention provides an artificial retinal prosthesis system, an extraocular optical device and an intraocular retina chip, wherein an optical modulation method converts image information into an optical pulse signal, and wherein the optical pulse signal is transmitted to the intraocular retina chip and decoded therein, whereby the intensity of the signal light is increased without decreasing contrast of the signal, and whereby superior imaging quality is achieved to support more related applications.

One embodiment of the present invention provides an artificial retinal prosthesis system, which comprises an extraocular optical device and an intraocular retina chip. The extraocular optical device includes an image capture module receiving external images and generating image signals; and a first signal processing module electrically connected with the image capture module, receiving the image signals, converting the image signals into optical pulse signals, and generating light energy. The intraocular retina chip includes a second processing module receiving the optical pulse signals and converting the optical pulse signals into control signals; a third processing module receiving the control signals and generating electric stimulation signals; and a solar cell module electrically connected with the second and third processing modules, receiving light energy, and converting the light energy into electric energy for powering the intraocular retina chip.

Another embodiment of the present invention provides an extraocular optical device, which applies to an artificial retinal prosthesis system and comprises an image capture module receiving external images and generating image signals; and a signal processing module electrically connected with the image capture module, receiving the image signals, and converting the image signals into optical pulse signals, wherein the optical pulse signals are generated via modulating the frequencies, amplitudes or phases of light pulses.

A further embodiment of the present invention provides an intraocular retina chip, which applies to an artificial retinal prosthesis system and comprises an optical pulse signal processing module receiving optical pulse signals and converting the optical pulse signals into control signals; an electric stimulation signal generating module receiving the control signals and converting the control signals into electric stimulation signals; and a solar cell module electrically connected with the optical pulse signal processing module and the electric stimulation signal generating module, receiving light energy, and converting the light energy into electric energy for powering the intraocular retina chip, wherein the optical pulse signals are generated via modulating the frequencies, amplitudes or phases of light pulses.

Below, embodiments are described in detail in cooperation with the attached drawings to make easily understood the objectives, technical contents, characteristics and accomplishments of the present invention.

DESCRIPTION OF THE PREFERRED EMBODIMENT

Below, preferred embodiments are described in cooperation with drawings to further demonstrate the present invention. However, it should be understood: these embodiments are only to exemplify the present invention but not to limit the scope of the present invention.

Figure 1:
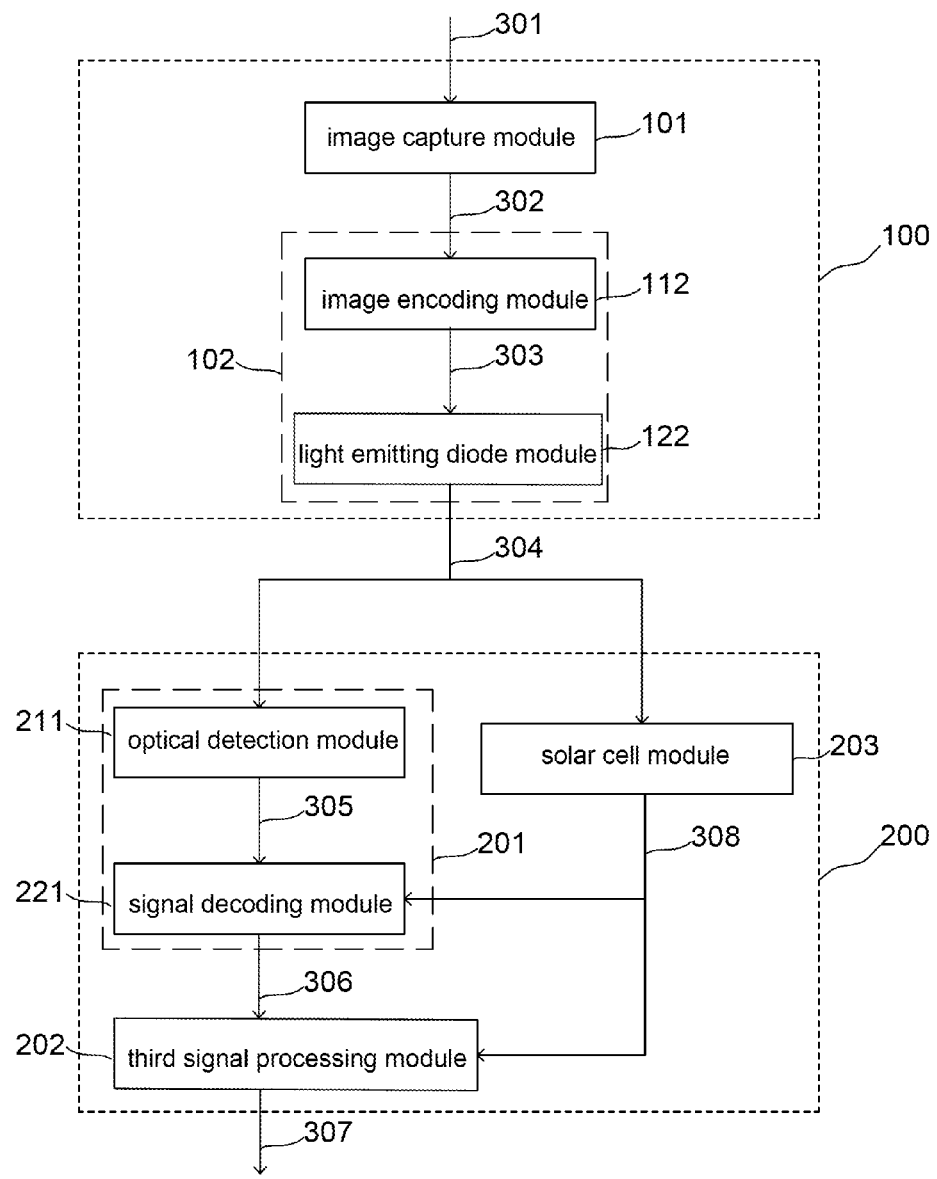
FIG. 1 is a block diagram schematically an artificial retinal prosthesis system according to one embodiment of the present invention.

Refer to FIG. 1. The artificial retinal prosthesis system 1000 of the present invention comprises an extraocular optical device 100 and an intraocular retina chip 200. In one embodiment, the intraocular retina chip 200 is a biomedicine chip implanted to the subretinal region in the eyeball. The extraocular optical device 100 includes an image capture module 101 and a first signal processing module 102 electrically connected with the image capture module 101. The image capture module 101 captures external images 301 and generates image signals 302. The first signal processing module 102 processes the image signals 302 and converts the image signals 302 into optical pulse signals 304. The external images 301 are visible lights or lights emitted by natural objects.

In one embodiment, the first signal processing module 102 further includes an image encoding module 112 and a light emitting diode (LED) module 122. The image encoding module 112 encodes the image signals 302 into transmittable signals 303. The LED module 122 receives the transmittable signals 303, converts the transmittable signals 303 into the optical pulse signals 304, and generates light energy (not shown in the drawings). It should be noted: the optical pulse signals are generated via modulating the frequencies, amplitudes or phases of light pulses. In one embodiment, the optical pulse signals include infrared light.

The optical pulse signals 304 generated by the extraocular optical device 100 are transmitted to the intraocular retina chip 200 inside the eyeball. In one embodiment, the intraocular retina chip 200 includes a second signal processing module 201, a third signal processing module 202 and a solar cell module 203, wherein the second signal processing module 201 further includes an optical detection module 211 and a signal decoding module 221. The optical detection module 211 converts the optical pulse signals 304, which is transmitted by the extraocular optical device 100, into electric signals 305. The signal decoding module 221 converts the electric signals 305 into control signals 306. Then, the third signal processing module 202 receives the control signals 306 and generates electric stimulation signals 307.

In one embodiment, the intraocular retina chip 200 includes a plurality of pixels, which jointly form the third signal processing module 202. Each pixel further includes an independent digital-analog converter, stimulator and an independent stimulation electrode. The stimulator converts the control signals 306 into stimulation currents having corresponding intensities. The stimulation electrode outputs the stimulation currents to form pixel electric stimulation signals (not shown in the drawings). The electric stimulation signals 307 are formed by the pixel electric stimulation signals, stimulating the nerve cells to generate vision.

The solar cell module 203 of the intraocular retina chip 200 is electrically connected with the second signal processing module 201 and the third signal processing module 202. In one embodiment, the solar cell module 203 is electrically connected with the signal decoding module 221 and the third signal processing module 202; the solar cell module 203 receives the light energy, which is transmitted by the extraocular optical device 100, and converts the light energy into electric energy 308 to power the intraocular retina chip 200.

Figure 2:
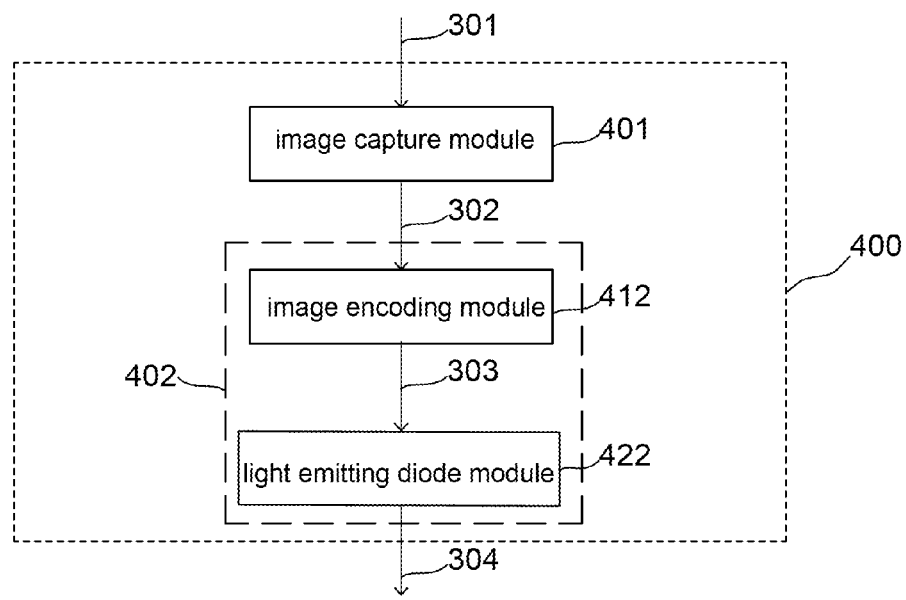
FIG. 2 is a block diagram schematically an extraocular optical device according to one embodiment of the present invention.

Refer to FIG. 2. Another embodiment of the present invention proposes an extraocular optical device 400, which applies to an artificial retinal prosthesis system and includes an image capture module 401 and a signal processing module 402. The image capture module 401 captures external images 301 and generates image information 302. The signal processing module 402 is electrically connected with the image capture module 401, receiving the image information 302 and converting the image information 302 into optical pulse signals 304. The signal processing module 402 further includes an image encoding module 412 and a light emitting diode (LED) module 422. The image encoding module 412 encodes the image information 302 into transmittable signals 303. The LED module 422 receives the transmittable signals 303, converts the transmittable signals 303 into optical pulse signals 304. It should be noted: the optical pulse signals are generated via modulating the frequencies, amplitudes or phases of light pulses. In one embodiment, the optical pulse signals include infrared light.

Figure 3:
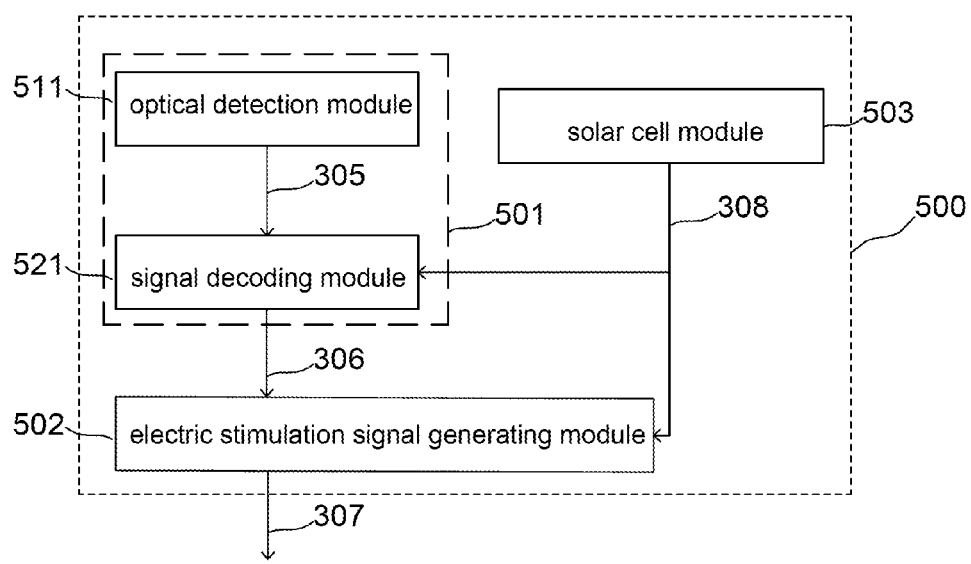
FIG. 3 is a block diagram schematically an intraocular retina chip according to one embodiment of the present invention.

Refer to FIG. 3. A further embodiment of the present invention proposes an intraocular retina chip 500, which applies to an artificial retinal prosthesis system and includes an optical pulse signal processing module 501, an electric stimulation signal generating module 502 and a solar cell module 503, wherein the optical pulse signal processing module 501 further includes an optical detection module 511 and a signal decoding module 521. The optical detection module 511 converts the external optical pulse signals (not shown in the drawing) into electric signals 305. The signal decoding module 521 converts the electric signals 305 into control signals 306. Then, the electric stimulation signal generating module 502 receives the control signals 306 and generates electric stimulation signals 307. It should be noted: the optical pulse signals are generated via modulating the frequencies, amplitudes or phases of light pulses. In one embodiment, the optical pulse signals include infrared light.

Figure 4:
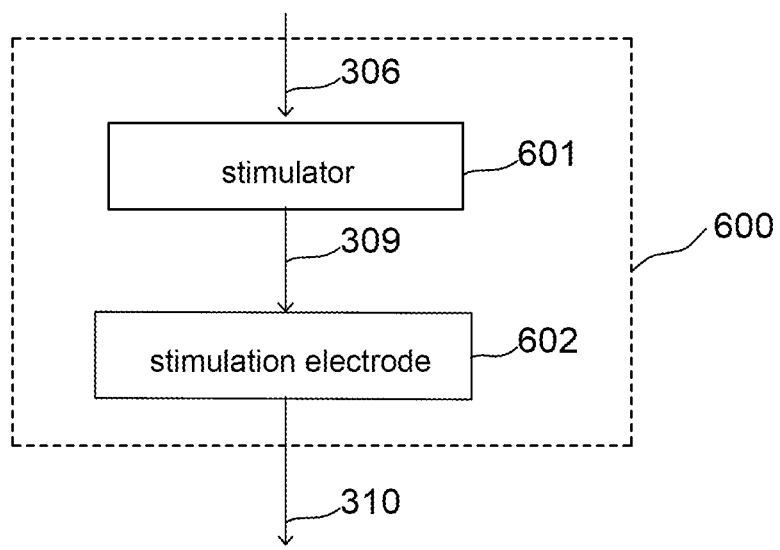
FIG. 4 is a block diagram schematically a pixel of an intraocular retina chip according to one embodiment of the present invention.

Refer to FIG. 4. In one embodiment, the intraocular retina chip 500 includes a plurality of pixels 600, which jointly form the electric stimulation signal generating module 502. Each pixel 600 further includes an independent digital-analog converter, stimulator 601 and an independent stimulation electrode 602. The stimulator 601 converts the control signals 306 into analog stimulation currents 309 having corresponding intensities. The stimulation electrode 602 outputs the stimulation currents 309 to form pixel electric stimulation signals 310. The electric stimulation signals 307 (shown in FIG. 3) are formed by the pixel electric stimulation signals 310, stimulating the nerve cells to generate vision.

Besides, the solar cell module 503 of the intraocular retina chip 500 is electrically connected with the optical pulse signal processing module 501 and the electric stimulation signal generating module 502. Preferably, the solar cell module 503 is electrically connected with the signal decoding module 521 and the electric stimulation signal generating module 502; the solar cell module 503 receives the external light energy and converts the external light energy into electric energy 308 to power the intraocular retina chip 500.

In conclusion, the present invention proposes an artificial retinal prosthesis system, an extraocular optical device and an intraocular retina chip, wherein external images are transmitted into the eyeball in form of optical pulse signals, and wherein the optical pulse signals are decoded and converted into corresponding electric stimulation currents stimulating nerve cells to form vision, and wherein the optical pulse signals also directly provide energy for the solar cell module to generate electric power, whereby the usage efficiency of the solar cells is promoted. Compared with the conventional artificial retinal prosthesis system, the present invention can acquire sufficient electric power, neither needing an additional light source (the background light) nor using a background light eliminator. The present invention can simplify the layout of the components and reduce the cost of the system without decreasing image contrast. Therefore, the present invention has high potential in the market.

What is claimed is:

1. An artificial retinal prosthesis system comprising
an extraocular optical device including
an image capture module receiving an external image and generating an image signal; and
a first signal processing module electrically connected with said image capture module, receiving said image signal, converting said image signal into an optical pulse signal, and generating light energy; and an intraocular retina chip including
- a second signal processing module receiving said optical pulse signal and converting said optical pulse signal into a control signal;
- a third signal processing module receiving said control signal and generating an electric stimulation signal; and
- a solar cell module electrically connected with said second signal processing module and said third signal processing module, receiving said light energy, and converting said light energy into electric power as a power source of said intraocular retina chip.

2. The artificial retinal prosthesis system according to claim 1, wherein said first signal processing module further includes
- an image encoding module encoding said image signal and generating a transmittable signal; and
- a light emitting diode module receiving said transmittable signal and converting said transmittable signal into said optical pulse signal.

3. The artificial retinal prosthesis system according to claim 2, wherein said optical pulse signal includes infrared light.

4. The artificial retinal prosthesis system according to claim 1, wherein said second signal processing module further includes
- an optical detection module receiving said optical pulse signal and converting said optical pulse signal into an electric signal; and
- a signal decoding module receiving said electric signal and converting said electric signal into said control signal.

5. The artificial retinal prosthesis system according to claim 1, wherein said intraocular retina chip includes a plurality of pixels each having a digital-analog converter, a stimulator and a stimulation electrode and jointly forming said third signal processing module, and wherein said digital-analog converter and said stimulator converts said control signal into a stimulation current having a relative intensity, and wherein said stimulation electrode outputs said stimulation current to generate an pixel electric stimulation signal, and wherein said electric stimulation signal is formed by said pixel electric stimulation signal.

6. The artificial retinal prosthesis system according to claim 1, wherein said optical pulse signal is generated via modulating frequencies, amplitudes and phases of light pulses.

* * * * *